(12) United States Patent
Krimsky

(10) Patent No.: US 10,470,839 B2
(45) Date of Patent: Nov. 12, 2019

(54) ASSESSMENT OF SUTURE OR STAPLE LINE INTEGRITY AND LOCALIZATION OF POTENTIAL TISSUE DEFECTS ALONG THE SUTURE OR STAPLE LINE

(71) Applicant: COVIDIEN LP, Mansfield, MA (US)

(72) Inventor: William S. Krimsky, Bel Air, MD (US)

(73) Assignee: COVIDIEN LP, Mansfield, MA (US)

( * ) Notice: Subject to any disclaimer, the term of this patent is extended or adjusted under 35 U.S.C. 154(b) by 788 days.

(21) Appl. No.: 15/171,727

(22) Filed: Jun. 2, 2016

(65) Prior Publication Data

US 2017/0348067 A1  Dec. 7, 2017

(51) Int. Cl.
| | | |
|---|---|---|
| A61B 90/00 | (2016.01) | |
| A61B 5/06 | (2006.01) | |
| A61B 34/10 | (2016.01) | |
| A61B 8/12 | (2006.01) | |
| A61B 8/00 | (2006.01) | |
| A61B 34/20 | (2016.01) | |

(52) U.S. Cl.
CPC .............. *A61B 90/37* (2016.02); *A61B 5/066* (2013.01); *A61B 8/12* (2013.01); *A61B 8/4254* (2013.01); *A61B 8/463* (2013.01); *A61B 34/10* (2016.02); *A61B 34/20* (2016.02); *A61B 2034/107* (2016.02); *A61B 2090/374* (2016.02); *A61B 2090/376* (2016.02); *A61B 2090/378* (2016.02); *A61B 2090/3762* (2016.02)

(58) Field of Classification Search
CPC ........ A61B 2034/107; A61B 2090/374; A61B 2090/376; A61B 2090/3762; A61B 2090/378; A61B 34/10; A61B 34/20; A61B 5/066; A61B 8/12; A61B 8/4254; A61B 8/463; A61B 90/37
See application file for complete search history.

(56) References Cited

U.S. PATENT DOCUMENTS

| | | | |
|---|---|---|---|
| 6,485,407 | B2 | 11/2002 | Alferness et al. |
| 6,491,706 | B1 | 12/2002 | Alferness et al. |
| 6,589,161 | B2 | 7/2003 | Corcoran |
| 6,599,311 | B1 | 7/2003 | Biggs et al. |

(Continued)

OTHER PUBLICATIONS

Alpert et al "Imaging the Post-Thoracotomy Patient". Radiol Clin N Am 52 (2014) 85-103 (Year: 2014).*

(Continued)

*Primary Examiner* — Michael T Rozanski

(57) ABSTRACT

A method for assessing suture line integrity includes loading a navigation plan into a navigation system, the navigation plan including a planned pathway shown in a 3D model, inserting a probe into a patient's airways, the probe including a location sensor in operative communication with the navigation system, registering a sensed location of the probe with the planned pathway, and selecting a target in the navigation plan, the target including a proposed suture line. The method further includes presenting a view of the 3D model showing the planned pathway and indicating the sensed location of the probe, navigating the probe through the airways of the patient's lungs toward the target, and imaging the proposed suture line of the target, via the probe, to determine tissue integrity surrounding the proposed suture line.

15 Claims, 6 Drawing Sheets

(56) References Cited

U.S. PATENT DOCUMENTS

| | | |
|---|---|---|
| 6,632,239 B2 | 10/2003 | Snyder et al. |
| 6,790,172 B2 | 9/2004 | Alferness et al. |
| 6,843,767 B2 | 1/2005 | Corcoran et al. |
| 6,860,847 B2 | 3/2005 | Alferness et al. |
| 6,997,189 B2 | 2/2006 | Biggs et al. |
| 7,100,616 B2 | 9/2006 | Springmeyer |
| 7,182,772 B2 | 2/2007 | Alferness et al. |
| 7,347,814 B2 | 3/2008 | Alferness et al. |
| 7,434,578 B2 | 10/2008 | Dillard et al. |
| 7,615,000 B2 | 11/2009 | Alferness et al. |
| 7,757,692 B2 | 7/2010 | Alferness et al. |
| 7,842,061 B2 | 11/2010 | Dillard et al. |
| 7,875,048 B2 | 1/2011 | Dillard et al. |
| 7,896,887 B2 | 3/2011 | Rimbaugh et al. |
| 8,021,385 B2 | 9/2011 | Alferness |
| 8,079,368 B2 | 12/2011 | Springmeyer |
| 8,147,532 B2 | 4/2012 | Barry et al. |
| 8,177,805 B2 | 5/2012 | Alferness |
| 8,257,381 B2 | 9/2012 | Dillard et al. |
| 8,322,335 B2 | 12/2012 | Barry et al. |
| 8,414,655 B2 | 4/2013 | Alferness et al. |
| 8,667,973 B2 | 3/2014 | Springmeyer |
| 8,734,380 B2 | 5/2014 | Barry et al. |
| 8,926,647 B2 | 1/2015 | Alferness |
| 8,956,319 B2 | 2/2015 | Dillard et al. |
| 8,974,484 B2 | 3/2015 | Alferness et al. |
| 8,986,336 B2 | 3/2015 | Rimbaugh et al. |
| 2004/0097983 A1 | 5/2004 | Snyder et al. |
| 2004/0220446 A1 | 11/2004 | Corcoran et al. |
| 2006/0212051 A1 | 9/2006 | Snyder et al. |
| 2007/0128174 A1 | 6/2007 | Kleinsek et al. |
| 2011/0081323 A1 | 4/2011 | Kleinsek et al. |
| 2011/0112573 A1 | 5/2011 | Bloom |
| 2014/0271531 A1 | 9/2014 | Freyman et al. |
| 2015/0073266 A1 | 3/2015 | Brannan et al. |
| 2015/0073268 A1 | 3/2015 | Stopek et al. |
| 2016/0000517 A1 | 1/2016 | Kehat et al. |

OTHER PUBLICATIONS

Canadian Office Action dated May 24, 2018 and issued in corresponding Canadian Patent Application No. 2,967,277.

Australian Examination Report dated Feb. 22, 2018 and issued in corresponding Australian Patent Application No. 2017202741.

Extended European Search Report dated Oct. 9, 2017 in corresponding European Patent Application No. 17173918.8, 7 pages.

\* cited by examiner

ASSESSMENT OF SUTURE OR STAPLE LINE INTEGRITY AND LOCALIZATION OF POTENTIAL TISSUE DEFECTS ALONG THE SUTURE OR STAPLE LINE

BACKGROUND

1. Technical Field

The present disclosure relates generally to treatment of patients with lung diseases, and, more particularly, to a system and method for assessing suture line or staple line integrity of a target or airway within a lung and localization of potential tissue defects along the suture line or staple line.

2. Discussion of Related Art

Lung cancer has an extremely high mortality rate, especially if it is not diagnosed in its early stages. The National Lung Screening Trial has demonstrated that a reduction in mortality occurs if diagnostic scans such as computed tomography (CT) scans are used for early detection for those at risk of contracting the disease. While CT scans increase the possibility that small lesions and nodules in the lung can be detected, these lesions and nodules still require biopsy and cytological examination before a diagnosis can be rendered and treatment can be undertaken.

Another major lung disease is chronic obstructive pulmonary disorder (COPD). One manifestation of COPD is emphysema. Poor airflow that results from emphysema is often the result of a breakdown of lung tissues. In patients suffering from emphysema the alveoli are no longer elastic and can become enlarged due to walls between the alveoli breaking down. As a result, the alveoli lose their shape and become floppy. This damage from emphysema leads to fewer and larger air sacs instead of many tiny ones. These large alveoli may be called bullae. One result of this breakdown of the alveoli is that the volume of gas exchange that can occur is reduced as the surface area of these fewer enlarged alveoli is less than the many smaller alveoli.

Additionally, the weakened floppy alveoli easily expand during an inhalation. Because of the weakened condition, the air having entered the weakened alveoli cannot be forced out of the lungs during exhalation. Deoxygenated air is trapped inside of the damaged floppy alveoli. This trapped air, however, keeps the alveoli expanded and thus takes up precious volume in the chest cavity. By taking up volume in the chest cavity, the volume available for inhalation of oxygenated air decreases, effectively preventing the patient from ever satisfying their need for oxygen. A patient suffering from emphysema will typically appear thin, and take very rapid low volume breaths. As can be imagined, the issue of easy filling and poor emptying of the lung leads to progressive hyper-expansion of the lungs, increased residual volume, reduced capacity, inefficient breathing mechanics, and in general, a continually worsening patient condition as they struggle to inspire sufficient volume of air. The classic description is that the patient will appear as a "pink puffer," because the patient will be constantly working in an effort to inspire any oxygen into their overinflated lung tissues.

Fully functioning alveoli can often adapt and at least partially compensate for the reduction in total lung capacity caused by emphysema, COPD, or lung cancer. Indeed, this is one reason for the use of Lung Volume Reduction Surgery (LVRS) where wedges of damaged lung are removed to allow the remaining tissue to function better. In part, this improved performance is enabled by the increase in space afforded the remaining alveoli to expand when the damaged portions of the lung are removed. By reducing the lung size, the remaining lung and surrounding muscles (intercostal and diaphragm) are able to work more efficiently. This makes breathing easier and helps patients achieve greater quality of life.

In the performance of LVRS, staples and sutures are used, primarily staples, to ligate the lung tissue and effectuate a seal. Occasionally, despite having been properly performed, a complete seal is not created, resulting in complications, including pneumothorax.

Accordingly, there is a need for systems and methods of confirming the integrity of suture and staples lines particularly in the lungs following procedures such as LVRS.

SUMMARY

In one aspect, the present disclosure is directed to a method for assessing suture line integrity. The method includes loading a navigation plan into a navigation system, the navigation plan including a planned pathway shown in a 3D model, inserting a probe into a patient's airways, the probe including a location sensor in operative communication with the navigation system, registering a sensed location of the probe with the planned pathway, and selecting a target in the navigation plan, the target including a proposed suture line. The method further includes the steps of presenting a view of the 3D model showing the planned pathway and indicating the sensed location of the probe, navigating the probe through the airways of the patient's lungs toward the target, and imaging the proposed suture line of the target, via the probe, to determine tissue integrity surrounding the proposed suture line.

In the disclosed embodiments, the method further comprises generating the 3D model from pre-procedure image data.

In the disclosed embodiments, the method further comprises assessing health of tissue proximate the proposed suture line.

In the disclosed embodiments, the method further comprises displaying one or more images of the proposed suture line on a display.

In the disclosed embodiments, the method further comprises imaging an actual suture line. The suture line is the result of a resection procedure.

In one aspect, the present disclosure is directed to a medical image display system. The medical image display system includes a network interface configured to receive positional information of a probe from a position sensor of the probe and image data from a navigation plan including a planned pathway of a lung, a memory storing the positional information, the image data, and instructions, a processor configured to execute the instructions, and a display configured to simultaneously display the positional information and image data. The instructions, when executed by the processor, cause the medical image display system to assess suture line integrity of a selected target in the navigation plan by allowing the probe to scan a suture line of the target to determine tissue integrity surrounding the suture line of the target.

In the disclosed embodiments, the image data is acquired by one or more imaging modalities. The imaging modalities are selected from the group comprising a CT scan, an X-ray scan, a computerized axial tomography (CAT) scan, a magnetic resonance imaging (MRI) scan, ultrasonography, contrast imaging, fluoroscopy, nuclear scans, and positron emission tomography (PET).

In the disclosed embodiments, the image data are selected from the group consisting of sagittal, coronal, and axial images.

In the disclosed embodiments, one or more images of the suture line of the target and the image data are controlled by a control function. The control function includes at least zooming and panning.

In the disclosed embodiments, the planned pathway is shown in a 3D model.

In the disclosed embodiments, the positional information and image data are dynamically displayed on the display.

In the disclosed embodiments, scanning the suture line of the target by the probe provides for predictive data used to determine the tissue integrity surrounding the suture line of the target.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
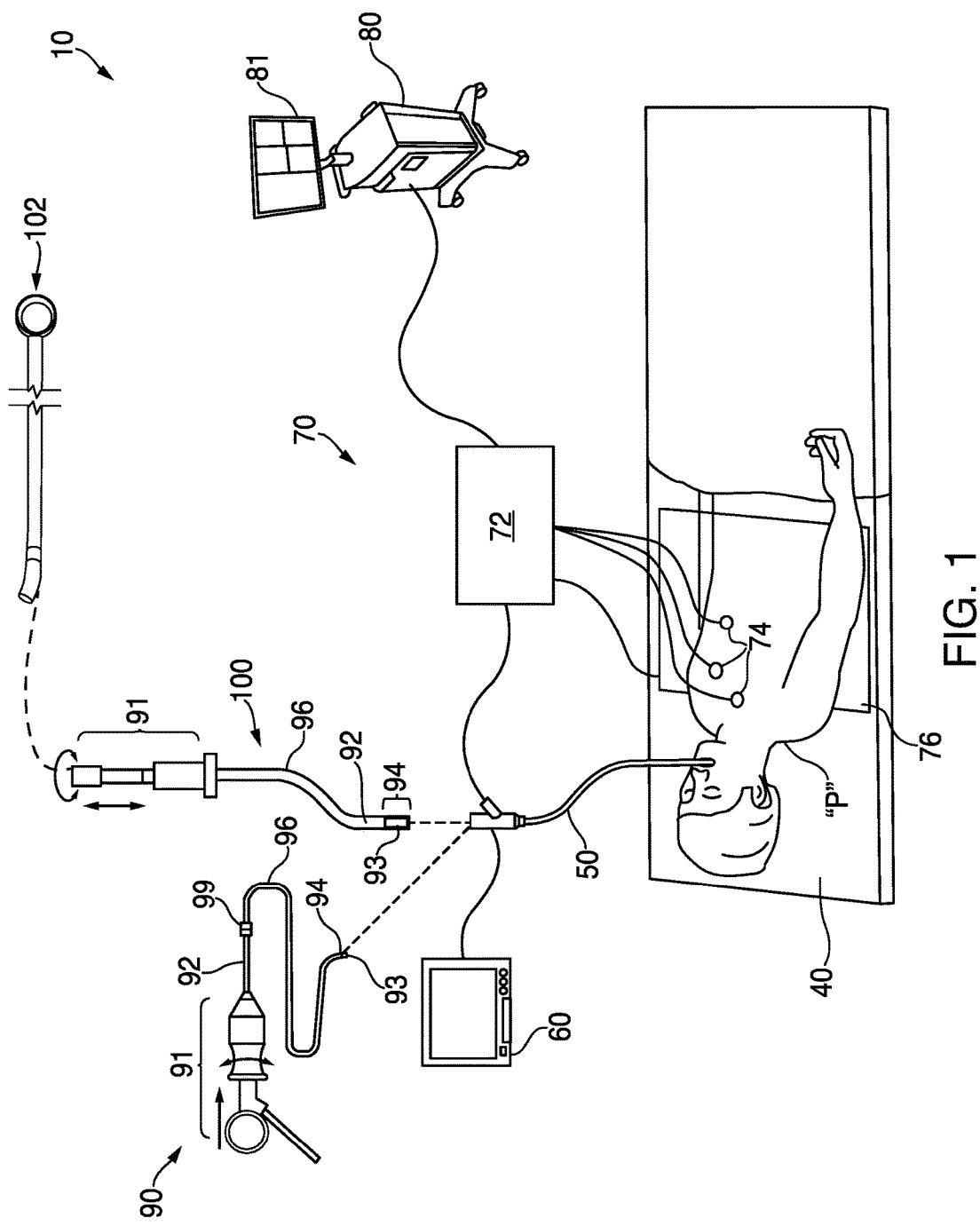
FIG. 1 is a system diagram of an example electromagnetic navigation (EMN) system, in accordance with aspects of the present disclosure.

Historically, surgical resection of diseased tissue has been performed using anatomic resection techniques. Challenges associated with these techniques are presented when margins are tight, tissue is flimsy or suturing/stapling is required of the major airways. Disruption of the suture line or staple line may result in bronchopleural fistulas. Thus, there is a desire to assess suture line or staple line integrity before sutures or staples are applied thereto and to present to the clinician multiple views of the suture line or staple line by using a combination of sensor data and imaging modality data.

In the present disclosure, the seal (e.g., suture line or staples) integrity testing may be done in the operating room during the initial procedure instead of having to subject the patient to another complete surgical prep and procedure in the event of failure of stitching, stapling or in the event of leakage necessary of repair. Further, because in larger part the integrity of the tissue itself serves to prevent the sutures or staples from tearing out of the tissue and compromising the seam before healing commences, the present disclosure provides a system and method that tests the tissue for integrity before the region is joined. These and other aspects of the present disclosure are detailed herein below.

Devices, systems, and methods for implementing a dynamic 3D lung map view for tool navigation inside a patient's lungs are provided in accordance with the present disclosure. A location sensor may be incorporated into different types of tools and catheters to track the location and assist in navigation of the tools. The tracked location of the location sensor may be used to visually show the location of a tool on the dynamic 3D lung map. The location of the location sensor within the body of a patient, with reference to a 3D map or 2D images, as well as a planned pathway assists the clinician in navigating lungs of the patient. Additionally, data/information collected via the location sensor of the different types of tools and catheters is automatically incorporated into the navigational software, in real-time, to continuously update variables/parameters associated with the navigational software. Thus, real-time data collection and real-time data processing provides for dynamic navigational software, which in turn provides for dynamic 3D lung mapping, as well as dynamic tool navigation techniques even if the area of interest is readily visible during routine inspection as this data provides the surgeon with information about surrounding structures, relative to the position of the defect or potential defect, etc. The data/information collected in real-time via the location sensor may be used, for example, to help the surgeon in determining the orientation of the tools, provide further information on surrounding structures, better plan for the type of intervention, etc. Therefore, the real-time feedback can influence how the surgeon proceeds with the surgical procedure.

The dynamic 3D lung map view, as disclosed herein, is one of a variety of views that may be presented by an electromagnetic navigation (EMN) system which may be used by a clinician to perform an ELECTROMAGNETIC NAVIGATION BRONCHOSCOPY® (ENB) procedure. Among other tasks that may be performed using the EMN system are planning a pathway to target tissue, navigating a positioning assembly to the target tissue, and navigating a variety of tools, such as a locatable guide (LG) and/or a biopsy tool to the target tissue.

An ENB procedure generally involves at least two phases: (1) planning a pathway to a target located within, or adjacent to, the patient's lungs; and (2) navigating a probe to the target along the planned pathway. These phases are generally referred to as (1) "planning" and (2) "navigation." An example of the planning software described herein can be found in U.S. Patent Application Nos. US 2014/0281961, US 2014/0270441, and US 2014/0282216, all of which are filed by Medtronic on Mar. 15, 2013 and entitled "Pathway Planning System and Method," all of which are incorporated herein by reference. An example of the planning software can be found in commonly assigned U.S. Provision Patent Application No. 62/020,240 entitled "SYSTEM AND METHOD FOR NAVIGATING WITHIN THE LUNG" the entire contents of which are incorporated herein by reference.

Prior to the planning phase, the patient's lungs are imaged by, for example, a computed tomography (CT) scan, although additional applicable methods of imaging will be known to those skilled in the art. The image data assembled during the CT scan may then be stored in, for example, the Digital Imaging and Communications in Medicine (DI-COM) format, although additional applicable formats will be known to those skilled in the art. The CT scan image data may then be loaded into a planning software application ("application") to be used during the planning phase of the ENB procedure.

The application may use the CT scan image data to generate a three-dimensional (3D) model of the patient's lungs. However, any other imaging modality may be used, as described below. The 3D model may include, among other things, a model airway tree corresponding to the actual airways of the patient's lungs, and showing the various passages, branches, and bifurcations of the patient's actual airway tree. Additionally, the 3D model may include lesions, markers, blood vessels, and/or a 3D rendering of the pleura. While the CT scan image data may have gaps, omissions, and/or other imperfections included in the image data, the 3D model is a smooth representation of the patient's airways, with any such gaps, omissions, and/or imperfections in the CT scan image data filled in or corrected. The 3D model may be viewed in various orientations. For example, if a clinician desires to view a particular section of the patient's airways, the clinician may view the 3D model represented in a 3D rendering and rotate and/or zoom in and/or pan in on the particular section of the patient's airways via a control function. Additionally, during the navigation phase of an ENB procedure, while a tool is being navigated through the patient's airways, the clinician may want to have the presented view of the 3D model dynamically updated as the tool is navigated.

During procedure planning, workstation 80 utilizes, for example, computed tomographic (CT) scan image data for generating and viewing a three-dimensional (3D) model of the patient's airways, enables the identification of target tissue on the 3D model (automatically, semi-automatically or manually), and allows for the selection of a pathway through the patient's airways to the target tissue. The 3D model may be presented on a display monitor associated with workstation 80, or in any other suitable fashion. In this fashion, the location of a proposed suture line for resection, as will be discussed in greater detail below, for a LVRS procedure may be identified. Indeed, in certain applications the target tissue is not diseased tissue but healthy tissue that can support suturing or stapling.

Using workstation 80, various views of the 3D model may be presented and may be manipulated by a clinician to facilitate identification of a target and selection of a suitable pathway through the patient's airways to access the target. For example, EMN application 81 may be configured in various states to display the 3D model in a variety of view modes. Some of these view modes may include a dynamic 3D lung map view. For each view of the 3D model, the angle from which the 3D model is displayed may correspond to a view point. The view point may be fixed at a predefined location and/or orientation, or may be adjusted by the clinician operating workstation 80.

As shown in FIG. 1, EMN system 10 generally includes an operating table 40 configured to support a patient "P"; a bronchoscope 50 configured for insertion through the patient's mouth and/or nose into the patient's airways; monitoring equipment 60 coupled to bronchoscope 50 for displaying video images received from bronchoscope 50; a tracking system 70 including a tracking module 72, a plurality of reference sensors 74, and an electromagnetic field generator 76; a workstation 80 including software and/or hardware, such as an EMN application 81, used to facilitate pathway planning, identification of target tissue, and navigation to the target tissue.

FIG. 1 also depicts two types of catheter guide assemblies 90, 100. Both catheter guide assemblies 90, 100 are usable with the EMN system 10 and share a number of common components. Each catheter guide assembly 90, 100 includes a handle 91, which is connected to an extended working channel (EWC) 96. EWC 96 is sized for placement into the working channel of bronchoscope 50. In operation, a locatable guide (LG) 92, including an electromagnetic (EM) sensor 94, is inserted into EWC 96 and locked into position such that the sensor 94 extends a desired distance beyond the distal tip 93 of EWC 96. The location of EM sensor 94, and thus the distal end of EWC 96, within an electromagnetic field generated by the electromagnetic field generator 76 can be derived by the tracking module 72, and the workstation 80. Catheter guide assemblies 90, 100 have different operating mechanisms, but each contain a handle 91 that can be manipulated by rotation and compression to steer the distal tip 93 of LG 92 and EWC 96. Catheter guide assemblies 90 are currently marketed and sold by Medtronic under the name SUPERDIMENSION® Procedure Kits, similarly catheter guide assemblies 100 are currently sold by Medtronic under the name EDGE™ Procedure Kits, both kits include a handle 91, EWC 96, and LG 92. For a more detailed description of the catheter guide assemblies 90, 100, reference is made to commonly-owned U.S. Patent Application Serial No. US 2014/0046315 entitled "MICROWAVE ABLATION CATHETER AND METHOD OF UTILIZING THE SAME", filed on Mar. 15, 2013 by Ladtkow et al., the entire contents of which are hereby incorporated by reference.

As illustrated in FIG. 1, the patient "P" is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, e.g., a video display, for displaying the video images received from the video imaging system of bronchoscope 50.

Catheter guide assemblies 90, 100 including LG 92 and EWC 96 are configured for insertion through a working channel of bronchoscope 50 into the patient's airways (although the catheter guide assemblies 90, 100 may alternatively be used without bronchoscope 50). LG 92 and EWC 96 are selectively lockable relative to one another via a locking mechanism 99. A six degrees-of-freedom electromagnetic tracking system 70, e.g., similar to those disclosed in U.S. Pat. No. 6,188,355 and published PCT Application Nos. WO 00/10456 and WO 01/67035, entitled "Wireless six-degree-of-freedom locator", filed on Dec. 14, 1998 by Gilboa, the entire contents of each of which is incorporated herein by reference, or any other suitable positioning measuring system, is utilized for performing navigation, although other configurations are also contemplated. Tracking system 70 is configured for use with catheter guide assemblies 90, 100 to track the position of EM sensor 94 as it moves in conjunction with EWC 96 through the airways of the patient "P," as detailed below.

As shown in FIG. 1, electromagnetic field generator 76 is positioned beneath the patient "P." Electromagnetic field generator 76 and the plurality of reference sensors 74 are interconnected with tracking module 72, which derives the location of each reference sensor 74 in six degrees of freedom. One or more of reference sensors 74 are attached to the chest of the patient "P." The six degrees of freedom coordinates of reference sensors 74 are sent to workstation 80, which includes EMN application 81 where sensors 74 are used to calculate a patient coordinate frame of reference.

Also shown in FIG. 1 is a tool 102 that is insertable into catheter guide assemblies 90, 100 following navigation to a target and removal of LG 92. The tool 102 may be a biopsy tool used to collect one or more tissue samples from the target tissue, a microwave ablation antenna, and others without departing from the scope of the present disclosure. In one embodiment, the tool 102 is an imaging tool that provides greater details about the tissue at the target. Tool 102 may be further configured for use in conjunction with tracking system 70 to facilitate navigation of tool 102 to the target tissue, and tracking of a location of tool 102 as it is manipulated relative to the target tissue. Tool 102 is referenced in specific embodiments herein below as imaging tool 102.

Moreover, data/information collected by the sensor 94 of the tool 102 may be automatically incorporated into the navigational software, in real-time, to continuously update variables/parameters associated with the navigational software. Thus, real-time data collection and real-time data processing provides for dynamic navigational software, which in turn provides for dynamic 3D lung mapping, as well as dynamic tool navigation techniques, even if the area of interest is readily visible during routine airway inspection given that which is outlined subsequently The data/information collected in real-time via the sensor 94 may be used, for example, to help the surgeon in determining the orientation of the tools, provide further information on surrounding structures, better plan for the type of intervention, etc. Therefore, the real-time feedback can influence how the surgeon proceeds with the surgical procedure. For instance, if tool 102 is a biopsy tool, the real-time data/information collected and processed may be used by the surgeon to determine different pathways to access the one or more desired tissue samples or may be used by the surgeon to determine which portion of the target tissue would provide for a better testing sample.

Although the EM sensor 94 is described above as being included in LG 92 it is also envisioned that EM sensor 94 may be embedded or incorporated within tool 102 where tool 102 may alternatively be utilized for navigation without need of LG 92 or the necessary tool exchanges that use of LG 92 requires. A variety of useable biopsy tools are described in U.S. Provisional Patent Application Nos. 61/906,732 and 61/906,762 both entitled "DEVICES, SYSTEMS, AND METHODS FOR NAVIGATING A BIOPSY TOOL TO A TARGET LOCATION AND OBTAINING A TISSUE SAMPLE USING THE SAME", filed Nov. 20, 2013 and U.S. Provisional Patent Application No. US 2015/0265257 having the same title and filed Mar. 14, 2014, the entire contents of each of which are incorporated herein by reference and useable with the EMN system 10 as described herein.

Following procedure planning, a procedure may be undertaken in which the EM sensor 94, in conjunction with tracking system 70, enables tracking of EM sensor 94 (and thus the distal end of the EWC or the tool 102) as EM sensor 94 is advanced through the patient's airways following the pathway planned during the procedure planning phase. Prior to the start of the navigation phase of an ENB procedure, the 3D model is registered with the actual lungs of the patient. One potential method of registration involves navigating a locatable guide into each lobe of the patient's lungs to at least the second bifurcation of the airways of that lobe. The position of the locatable guide is tracked during this registration phase, and the 3D model is iteratively updated based on the tracked position of the locatable guide within the actual airways of the patient's lungs. This registration process is described in commonly-owned U.S. Provisional Patent Application Ser. No. 62/020,220 entitled "Real-Time Automatic Registration Feedback", filed on Jul. 2, 2014, by Brown et al. With reference to FIG. 1, an EMN system 10 is provided in accordance with the present disclosure. One such EMN system is the ELECTROMAGNETIC NAVIGATION BRONCHOSCOPY® system currently sold by Medtronic.

Figure 2:
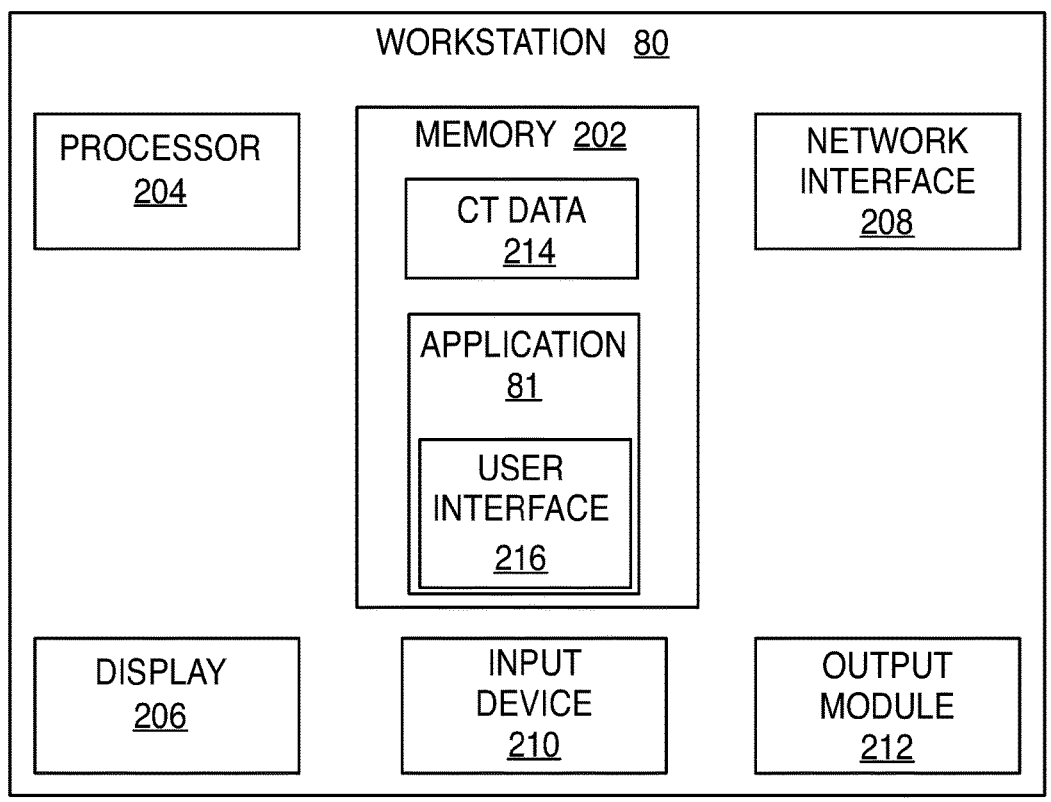
FIG. 2 depicts a schematic diagram of an example workstation forming part of the EMN system of FIG. 1, in accordance with aspects of the present disclosure.

Turning now to FIG. 2, there is shown a system diagram of workstation 80. Workstation 80 may include memory 202, processor 204, display 206, network interface 208, input device 210, and/or output module 212. Memory 202 may store EMN application 81 and/or CT data 214. EMN application 81 may, when executed by processor 204, cause display 206 to present user interface 216. The EMN application 81 provides the interface between the sensed position of the EM sensor 94 and the image and planning data developed in the planning phase.

Figure 3:
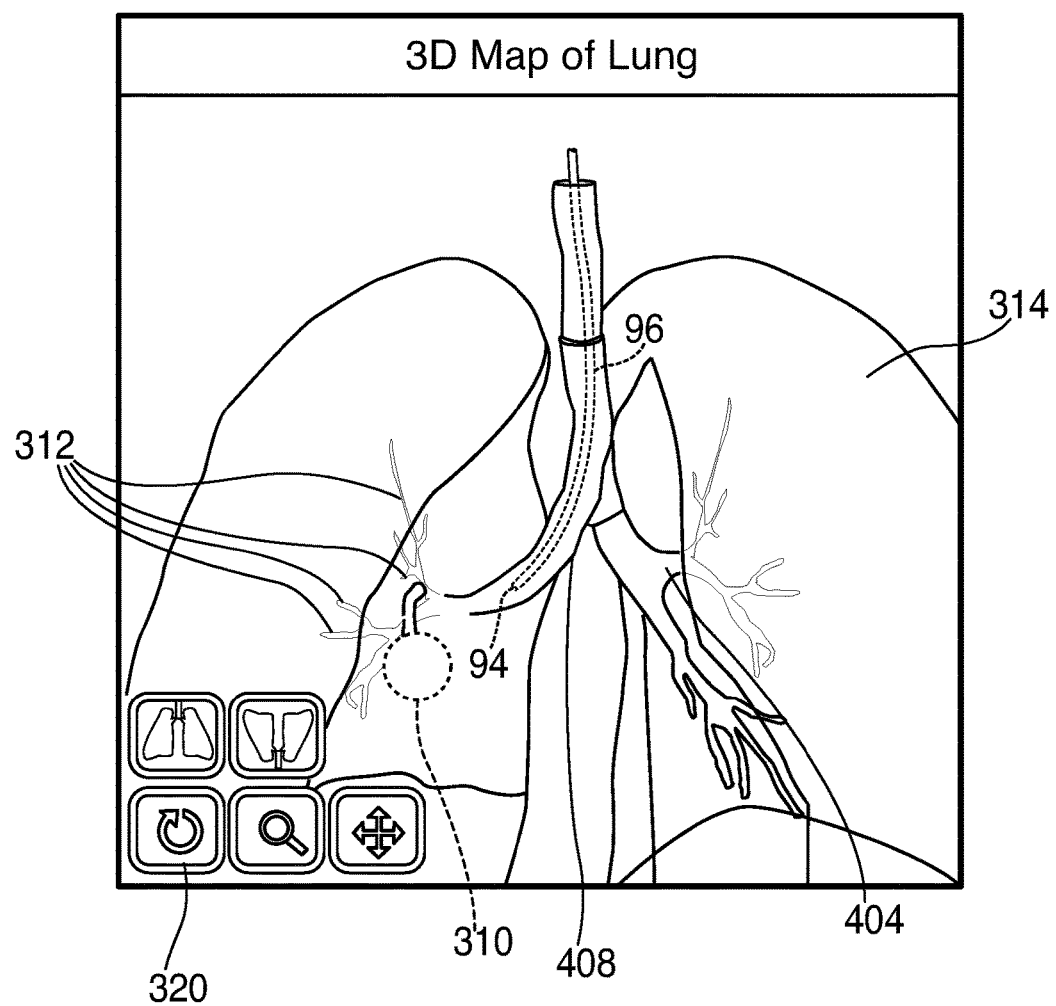
FIG. 3 is an example view of a user interface that may be presented on the workstation of FIG. 2 showing an example of a 3D map of a lung, in accordance with aspects of the present disclosure.

FIG. 3 is an example view of a user interface that may be presented on the workstation of FIG. 2 showing an example of a 3D map of a lung, in accordance with aspects of the present disclosure.

The 3D lung map view shows a representation of the EWC 96 and the EM sensor 94 of LG 92 associated with the EWC 96 within the patient's airways. Also shown by the 3D lung map view are the airway tree 404, the pathway 408, the target 310, the surrounding airways 312, and the pleura 314 of the lungs. The 3D map view also depicts a plurality of buttons 320 for adjusting characteristics of the 3D lung map.

Figure 4:
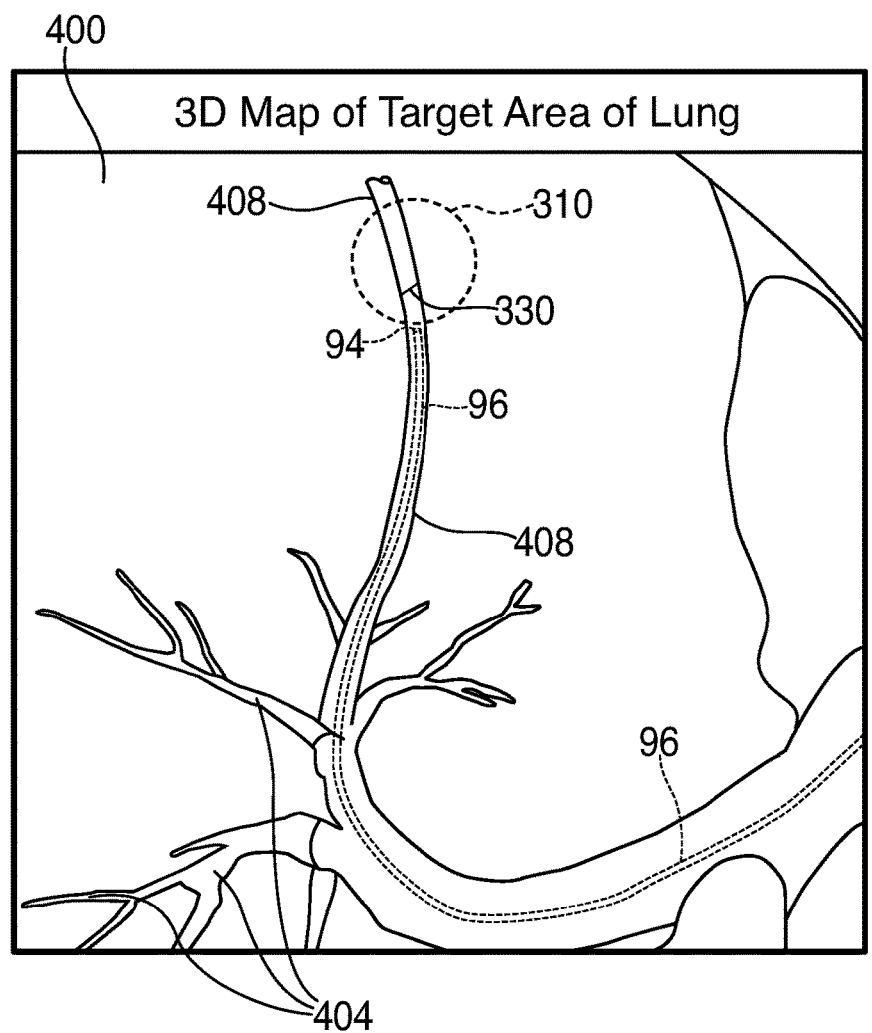
FIG. 4 is an example view of a user interface that may be presented on the workstation of FIG. 2 showing an example of a target area of a lung having a suture line, in accordance with aspects of the present disclosure.

FIG. 4 is an example view of a user interface 400 that may be presented on the workstation of FIG. 2 showing an example of a target area 310 of a lung having a proposed suture line 330, in accordance with aspects of the present disclosure. Though depicted here schematically affecting a single airway 404, one of skill in the art will recognize that in accordance with an LVRS procedure the proposed suture line 330 may extended across multiple airways and blood vessels. Further the proposed suture line 330 may be formed by using staples and staplers such as the suite of open and laparoscopic staplers currently marketed and sold by Medtronic for stapling and resecting tissue.

User interface 400 shows the EWC 96 and EM sensor 94 within airway tree 404, during the navigation along pathway 408. The clinician may zoom in and out of one or more areas of interest within the lungs via a control function. The 3D map of the lungs may thus be a dynamic 3D map of the lungs, which is continuously updated and/or adjusted during the navigation procedure.

Upon arriving proximate the location of the proposed suture line 330, as confirmed by the EMN system 10 described above, the clinician may remove the EM sensor 94 and LG 92 from the EWC 96 and insert the tool 102. Specifically tool 102 is an imaging tool 102, such as an ultrasound (US) imaging probe or an optical coherence tomography (OCT) probe into the EWC 96. In further embodiments, the EM sensor 94 is incorporated into the EWC 96 or the imaging device such that removal of the LG 92 is obviated. Once placed proximate the location of the proposed suture line 330, images of the location may be acquired to assess the viability of the location for placement of sutures or staples, such as for an LVRS procedure.

Figure 5A:
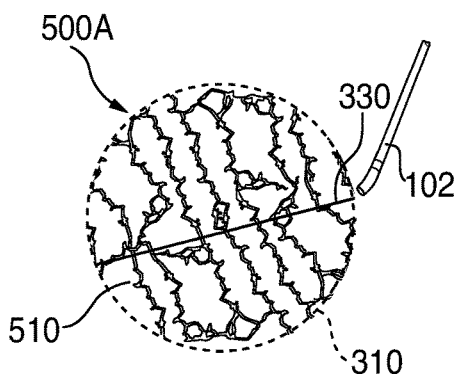
FIG. 5A is an enlarged view of a target area of a lung having a suture line, the target area composed of healthy tissue, in accordance with aspects of the present disclosure.

FIG. 5A is an image 500A of target area 310 as imaged by imaging tool 102 extending from LG 96. By determining the location of the imaging tool 102, the EMN application 81 may overlay the proposed suture line 330 on the image 500A.

As depicted in FIG. 5A, the imaging device 102 may be moved along the proposed suture line 330 (FIG. 5E) to scan or examine or inspect or evaluate or review or investigate or analyze or assess the tissue surrounding the proposed suture line 330. Scanning of the proposed suture line 330 in FIG. 5A with imaging tool 102 may reveal that the tissue surrounding the proposed suture line 330 is comprised of healthy tissue 510. Thus, the tissue surrounding the proposed suture line 330 does not present any flaws (e.g., too fragile, structural defects, bleeding, etc.) that would cause future disruptions of the suture line. Consequently, a clinician may proceed to apply sutures or staples to the proposed suture line 330 with a high degree of confidence that the suture line will remain intact intra-operatively, as well as post-operatively. In this way, the scanning of the suture line 330 provides the clinician with predictive data in regards to a probability of failure of the suture line 330. The predictive data also includes the location of where the failure of the suture line 330 may occur.

Figure 5B:
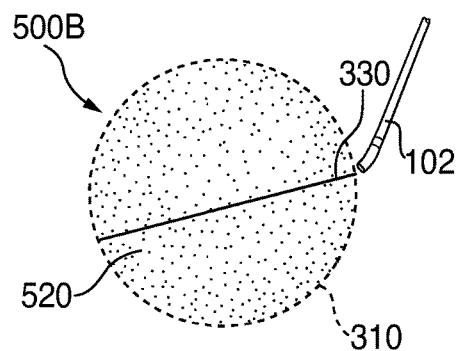
FIG. 5B is an enlarged view of a target area of a lung having a suture line, the target area composed of diseased tissue, in accordance with aspects of the present disclosure.

In FIG. 5A, there is no location along the proposed suture line 330 that would indicate any likelihood of failure. In FIG. 5B the target area 310 is composed solely of diseased tissue 520. Thus, the tissue surrounding the proposed suture line 330 presents flaws (e.g., too fragile, structural defects, bleeding, etc.) that would cause future disruptions of the suture line. Consequently, a clinician may determine not to proceed with application of sutures or staples to the proposed suture line 330 since there is a high degree of likelihood that the proposed suture line 330 will not remain intact either intra-operatively or post-operatively. In this way, the scanning of the proposed suture line 330 provides the clinician with predictive data in regards to a probability of failure of the proposed suture line 330.

Figure 5C:
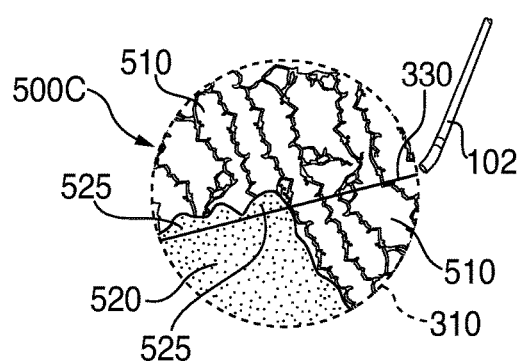
FIGS. 5C-5D are enlarged views of a target area of a lung having a suture line, the target area composed of healthy and diseased tissue, in accordance with aspects of the present disclosure.
Figure 5D:
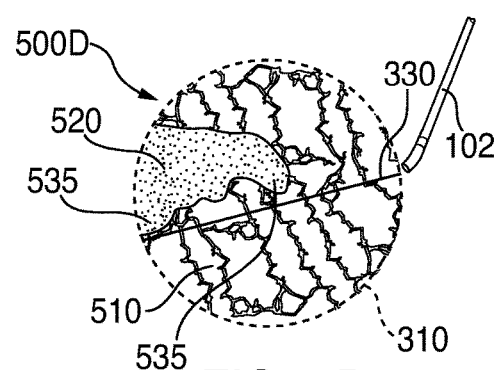

The predictive data may also include the location of where the failure of the suture line 330 may occur. In FIG. 5B, the suture line 330 would indicate a likelihood of failure across its entire length. In FIGS. 5C-5D the target area 310 is composed of healthy and diseased tissue 510, 520.

In FIG. 5C, scanning of the proposed suture line 330 with imaging tool 102 would reveal that a portion of the tissue (i.e., tissue region 525) surrounding the suture line 330 is diseased tissue 520. Thus, the tissue region 525 surrounding a portion of the suture line 330 presents flaws that could cause future disruptions of the suture line. Consequently, a clinician may determine not to proceed with application of sutures to the suture line 330 since there is a high degree of likelihood that the suture line 330 will not remain intact.

In FIG. 5D, scanning of the proposed suture line 330 with imaging tool 102 would reveal that a portion of the tissue (i.e., tissue region 535) in proximity to the proposed suture line 330 is diseased tissue 520. Thus, tissue region 535 that is in proximity to the proposed suture line 330 may present flaws that would cause future disruptions of the suture line 330. Consequently, a clinician may determine not to proceed with application of sutures to the suture line 330 since there is some degree of likelihood that the proposed suture line 330 will not remain intact either intra-operatively or post-operatively. However, depending on the distance between the proposed suture line 330 and the tissue region 535, a clinician may determine to proceed with application of sutures to the proposed suture line 330 since the risk of failure may be determined by the clinician to be low. Thus, in this instance, the clinician's prior experience may dictate whether such application of sutures to proposed suture line 330 within a certain distance of tissue region 535 will result in successful application of a suture.

In this way, in FIGS. 5C and 5D, the scanning of the proposed suture line 330 provides the clinician with predictive data in regards to a probability of failure of the proposed suture line 330. The predictive data also includes the location of the where the failure of the proposed suture line 330 may occur. In FIG. 5C, the proposed suture line 330 would indicate a likelihood of failure in region 525, whereas in FIG. 5D, the proposed suture line 330 may indicate a low likelihood of failure near region 535 based on the distance of the proposed suture line 330 from the tissue region 535. This distance may be provided to the clinician by EMN application 81 to assist the clinician in making a determination of a probability of failure or success of maintaining the suture line integrity based on that distance.

Figure 5E:
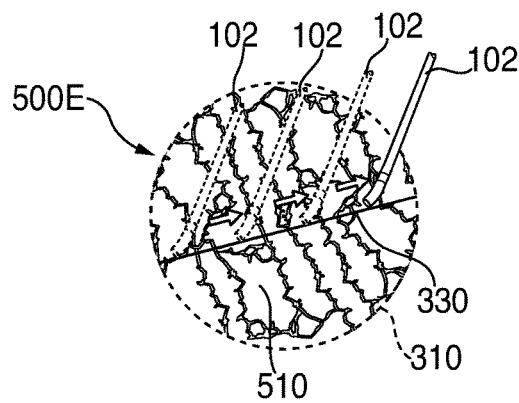
FIG. 5E is an enlarged view of a target area of a lung having a suture line, the suture line scanned by a probe or imaging tool for assessment of tissue integrity, in accordance with aspects of the present disclosure.

For illustrative purposes, FIG. 5E shows movement of the imaging tool 102 along the proposed suture line 330. The clinician may move imaging device in any direction in order to scan or examine or inspect or evaluate or investigate or assess the integrity of tissue around the proposed suture line 330. Several images and/or data may be acquired from the scanning of the imaging tool 102 around the proposed suture line 330. Thus, the integrity of the tissue itself serves to prevent sutures or staples from tearing out of the tissue and compromising the seam before healing commences. As a result, the present disclosure provides a system and method that test an anastomosis for integrity before the region is joined by either sutures or staples.

Having navigated the EWC 96 and the imaging tool 102 proximate the proposed suture line 330, and having made an assessment of the integrity of the tissue, the clinician may now proceed to perform a resection (e.g., a LVRS). Following completion of the resection, the EWC 96 and the imaging tool 102 may be navigated back to the target site 310. In practice, this may be a very short navigation with the EWC 96 and the imaging tool 102 having only been retracted sufficiently to not interfere with the resection tools (e.g., staplers and the like).

Returning to the site of the resection, the proposed suture line 330 is now replaced with an actual suture line 332 (FIG. 7), which is visible in the images generated by the imaging tool 102. By reviewing these images, the clinician is able to make an assessment of the efficacy and integrity of the actual suture line 332. By imaging the suture line 332, the clinician can determine if the suture line 332 is complete and also assess whether there is unexpected bleeding, or other imperfections in the suture line 332 that might result in a less than desired seal of the airway 404. For example, the images returned by imaging tool 102 may reveal that some of the sutures have pulled through the tissue, alternatively, the images may reveal that staples were not completely compressed, or that the entirety of the airway was not closed. These and other imperfections may be assessed during the LVRS or resection procedure enabling the clinician to undertake immediate intervention and corrective actions, including, but not limited to additional suturing or stapling, electro-cauterization and vessel sealing of unsealed blood vessels, and further resection if it is determined that the suture line 332 is not placed in tissue of sufficient integrity.

Figure 6:
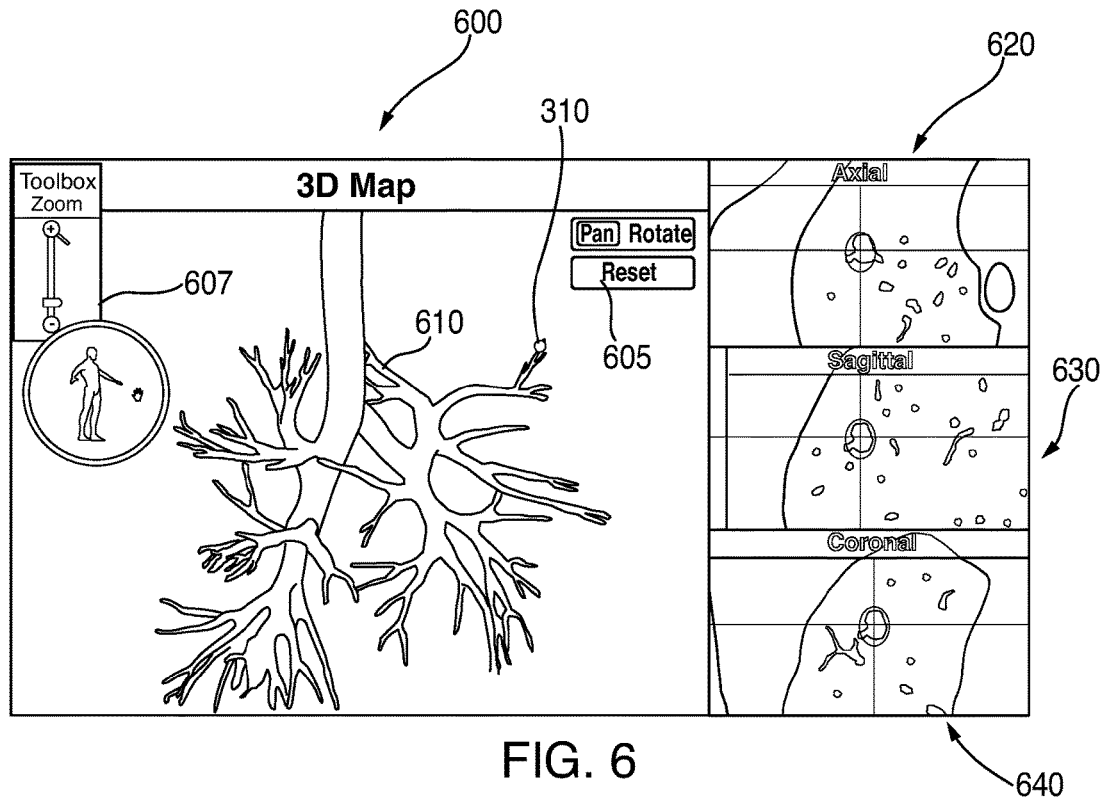
FIG. 6 is an example view of a user interface that may be presented on the workstation of FIG. 2 showing an example of a 3D map of a lung having a target area, as well as axial, sagittal, and coronal views of the target area, in accordance with aspects of the present disclosure.

FIG. 6 is a further example of a user interface 600 that may be presented on the workstation of FIG. 2 showing an example of a 3D map of a lung having target area 310, as well as axial, sagittal, and coronal views 620, 630, 640 of the target area 310, in accordance with aspects of the present disclosure. User interface 600 may be presented either in the planning phase or in the navigation phase of the procedures described herein. That is, a clinician may be presented with the user interface 600 when determining where to place the proposed suture line 330, when actually assessing the proposed suture line 330 following a pathway plan to the target 310, and when re-navigating to the target 310 following resection of tissue to assess an actual suture line 332. The user interface 600 further depicts buttons 605 for manipulating the 3D map of the airway 610. The user interface 600 also depicts a toolbar zoom function 607 (or control function) for zooming in and out of, for example, the target area 310.

As described above, the 3D model of the airway 610 is generated from an image data such as CT images. The EMN application 81 allows for the image data to both be rendered into a 3D model and also displayed as individual 2D image slices of different views including axial, coronal, and sagittal views 620, 630, 640 that are commonly used to review the original image data. These different views allow the clinician or user to review further details the image data and identify potential targets in the images and to make assessments of potential sites for a proposed suture line 330.

Figure 7:
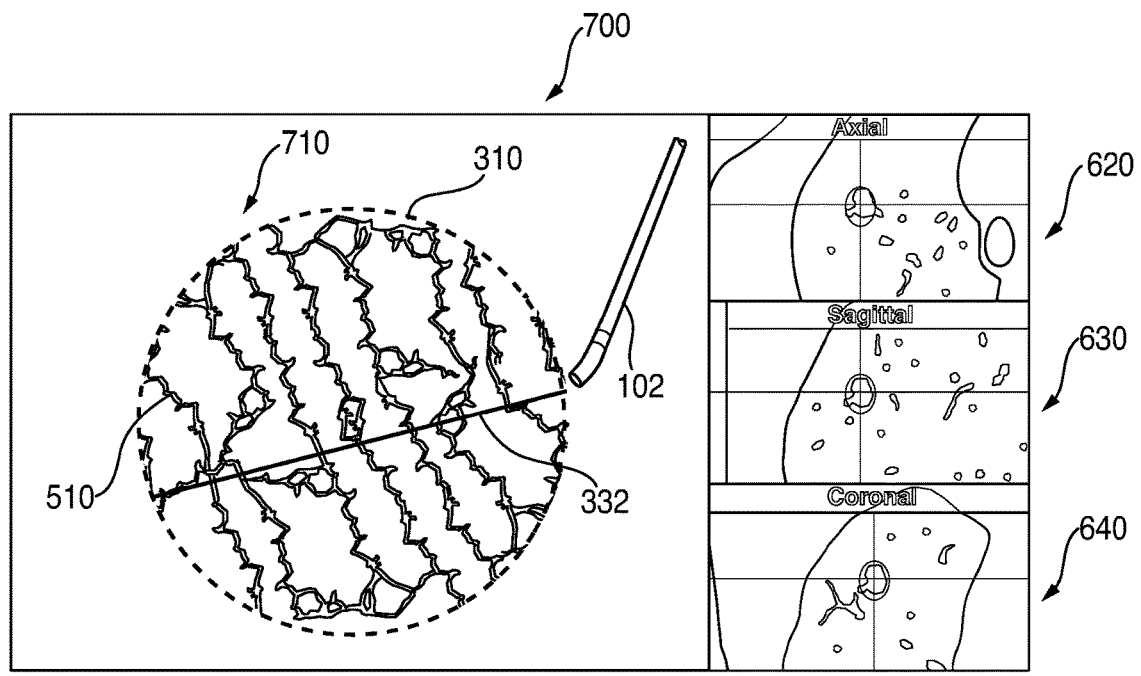
FIG. 7 is an example view of a user interface that may be presented on the workstation of FIG. 2 showing an example of the target area having the suture line, as well as axial, sagittal, and coronal views of the target area, in accordance with aspects of the present disclosure.

FIG. 7 is an example view of a user interface 700 that may be presented on the workstation of FIG. 2 showing an example of target area 310 following navigation and imaging using the imaging tool 102. The use interface 700 may depict proposed suture line 330, as well as axial, sagittal, and coronal views 620, 630, 640 of target area 310, in accordance with aspects of the present disclosure when making assessments of the integrity of the tissue of a proposed suture line 330. Similarly, user interface 700 may depict an actual suture line 332 as imaged by imaging tool 102 following a resection procedure so that the clinician may undertake the assessment of the suture line as described herein.

In FIG. 7, the dynamic 3D model 610 of FIG. 6 has been replaced with the image 710 received from the imaging tool 102. This image may show either the proposed suture line 330 or the actual suture line 332. The user interface 700 may alternatively depict the 3D model 610 and the image 710 simultaneously and with axial, sagittal, and coronal views 620, 630, 640 of the target area 310.

Therefore, with regard to FIGS. 6 and 7, the clinician may view images from imaging tool 102 to assess the proposed suture line 330 and the actual suture line 332, as well as the axial, sagittal, and coronal images 620, 630, 640 derived from positional information of the position sensor 94 of the navigation instrument 100 (FIG. 1) in order to make clinical decisions regarding the resection procedure. Further, through the use of the EMN system 10, changes in the positional information indicating movement of the position sensor 94 can also be displayed.

Referring back to FIG. 1, the tracking module 72 receives the positional information from the sensor 94 associated with the navigation instrument 100 and the reference sensors 74 to identify the location of the sensor 94 within the patient "P," and associate that position with 2-dimensional images and 3-dimensional maps to enable navigation of the navigation instrument 100 within the patient "P." The positional information is identified in the coordinate system of the 3D map so that the user interfaces 600, 700 may be able to display the position of the sensor 94 in the 3D map. Additionally, axial, sagittal, and coronal images 620, 630, 640 are derived from the position sensor 94. The axial, sagittal, and coronal images 620, 630, 640 may then be simultaneously displayed with the images received from the imaging tool 102 scanning the suture line 330.

Thus, the clinician may evaluate whether a proposed suture line 330 or staple line has sufficient integrity from a combination of the data derived from the image data used to generate the 3D model and the data derived from the imaging tool 102 scanning the tissue of a proposed suture line 330 or actual suture line 332 for enhanced localization and pinpointing of potential defects. In this way, the clinician may both predict, based on this combination of data, whether the potential application of sutures to the suture line or staples to the staple line would result in disruption of the suture line or staple line, as well as make post suturing or stapling assessments. The result being the reduction in negative outcomes such as the formation of bronchopleural fistulas.

In an aspect, the number of windows displayed on the user interfaces 600, 700 of FIGS. 6 and 7 may be automatically adjusted based on the procedural mode and the positional information of the sensor 94. Clinicians may also manually remove a window from the user interfaces 600, 700 and add one or more windows to the user interfaces 600, 700. The number of windows displayed on the user interfaces 600, 700, however, may not be limited to a predetermined number but can be increased or decreased based on the real estate of the user interfaces 600, 700, the mode, and/or a clinician's preference. In an embodiment, clinicians may manually switch the locations of any windows described above, stack them vertically, increase or decrease the size of the windows, and add or remove any windows.

With respect to memory 202 described above in connection with FIG. 2, the memory 202 may include any non-transitory computer-readable storage media for storing data and/or software that is executable by processor 204 and which controls the operation of workstation 80. In an embodiment, memory 202 may include one or more solid-state storage devices such as flash memory chips. Alternatively or in addition to the one or more solid-state storage devices, memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 80.

Network interface 208 may be configured to connect to a network such as a local area network (LAN) consisting of a wired network and/or a wireless network, a wide area network (WAN), a wireless mobile network, a Bluetooth network, and/or the internet. Input device 210 may be any device by means of which a user may interact with workstation 80, such as, for example, a mouse, keyboard, foot pedal, touch screen, and/or voice interface. Output module 212 may include any connectivity port or bus, such as, for example, parallel ports, serial ports, universal serial busses (USB), or any other similar connectivity port known to those skilled in the art.

Detailed embodiments of devices, systems incorporating such devices, and methods using the same as described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in appropriately detailed structure. While the preceding embodiments are described in terms of bronchoscopy of a patient's airways, those skilled in the art will realize that the same or similar devices, systems, and methods may be used in other lumen networks, such as, for example, the vascular, lymphatic, and/or gastrointestinal networks as well.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A method for assessing suture line integrity, the method comprising:
   receiving a navigation plan into a navigation computer, the navigation plan including a planned pathway shown in a 3D model;
   registering a sensed location of a probe within a patient's airways with the planned pathway, the probe including a location sensor in communication with the navigation computer;
   displaying a line to be sutured over a target identified in the navigation plan;
   presenting a view of the 3D model showing the planned pathway and indicating the sensed location of the probe;
   receiving image data of tissue surrounding the line to be sutured from the probe within the patient's airways; and
   determining integrity of the tissue surrounding the line to be sutured based on the received image data.

2. The method according to claim 1, further comprising generating the 3D model from pre-procedure image data.

3. The method according to claim 1, further comprising assessing health of the tissue surrounding the line to be sutured.

4. The method according to claim 1, further comprising displaying one or more images of the line to be sutured on a display.

5. The method according to claim 4, further comprising imaging an actual suture line.

6. A medical image display system, comprising:
   a network interface configured to receive positional information of a probe from a position sensor of the probe and image data from a navigation plan including a planned pathway of a lung;
   a memory storing the positional information, the image data, and instructions;
   a processor configured to execute the instructions; and
   a display configured to simultaneously display the positional information and image data;
   wherein the instructions, when executed by the processor, cause the medical image display system to:
      display a line to be sutured over a target identified in the navigation plan;
      image tissue surrounding the line to be sutured by allowing the probe to scan the tissue surrounding the line to be sutured and integrity of the tissue surrounding the line to be sutured based on the imaged tissue.

7. The system according to claim 6, wherein the image data is acquired by one or more imaging modalities.

8. The system according to claim 7, wherein the imaging modalities are selected from the group comprising a CT scan, an X-ray scan, a computerized axial tomography (CAT) scan, a magnetic resonance imaging (MRI) scan, ultrasonography, contrast imaging, fluoroscopy, nuclear scans, and positron emission tomography (PET).

9. The system according to claim 6, wherein the image data are selected from the group consisting of sagittal, coronal, and axial images.

10. The system according to claim 6, wherein one or more images of the tissue surrounding the line to be sutured and the image data are controlled by a control function.

11. The system according to claim 10, wherein the control function includes at least zooming and panning.

12. The system according to claim 6, wherein the planned pathway is shown in a 3D model.

13. The system according to claim 6, wherein the positional information and image data are dynamically displayed on the display.

14. The system according to claim 6, wherein allowing the probe to scan the tissue surrounding the line to be sutured provides for predictive data used to determine the integrity of the tissue surrounding the line to be sutured.

15. A medical image display system, comprising:
   a memory storing instructions, positional information of a probe navigated within a patient, and a navigation plan including a planned pathway through a patient's airways;
   a processor configured to execute the instructions; and
   a display configured to display the planned pathway and the positional information of the probe;
   wherein the instructions, when executed by the processor, cause the medical image display system to:
      display a line to be sutured over a target identified in the navigation plan;
      receive image data of tissue surrounding the line to be sutured from the probe; and
      determine integrity of the tissue surrounding the line to be sutured based on the image data received from the probe.

* * * * *